United States Patent

Dauth et al.

[11] Patent Number: 6,100,348
[45] Date of Patent: Aug. 8, 2000

[54] CROSSLINKABLE COMPOSITIONS

[75] Inventors: Jochen Dauth; Bernward Deubzer, both of Burghausen; Josef Wolferseder, Tann; Klaus Schnitzer, Julbach, all of Germany

[73] Assignee: Wacker-Chemie GmbH, München, Germany

[21] Appl. No.: 09/088,518

[22] Filed: Jun. 2, 1998

[30] Foreign Application Priority Data

Jun. 5, 1997 [DE] Germany .............. 197 23 669

[51] Int. Cl.$^7$ .............. C08F 283/00; C08F 30/08; C08G 77/12; C08G 77/20; B32B 9/04

[52] U.S. Cl. .............. 525/478; 525/42; 526/279; 528/31; 528/32; 428/447

[58] Field of Search .............. 526/279; 525/42, 525/478; 428/447; 528/31, 32

[56] References Cited

U.S. PATENT DOCUMENTS

| | | |
|---|---|---|
| 2,813,218 | 11/1957 | Kloepping et al. . |
| 3,192,181 | 6/1965 | Moore .............. 26/46.5 |
| 3,249,581 | 5/1966 | Nelson et al. . |
| 3,344,111 | 9/1967 | Chalk et al. .............. 260/46.5 |
| 3,383,356 | 5/1968 | Nielson .............. 260/46.5 |
| 3,436,366 | 4/1969 | Modic et al. . |
| 3,445,420 | 5/1969 | Kookootsedes et al. .............. 260/37 |
| 3,882,083 | 5/1975 | Berger et al. .............. 528/15 |
| 4,292,434 | 9/1981 | Lindner et al. . |
| 4,595,739 | 6/1986 | Cáuezzan . |
| 4,670,531 | 6/1987 | Eckberg . |
| 5,082,871 | 1/1992 | Eckberg . |
| 5,241,034 | 8/1993 | Herzig et al. . |
| 5,629,387 | 5/1997 | Frances et al. . |
| 5,872,274 | 2/1999 | Cannady et al. . |

FOREIGN PATENT DOCUMENTS

| | | |
|---|---|---|
| 0110370 | 11/1983 | European Pat. Off. . |
| 0 405 560 A2 | 1/1991 | European Pat. Off. . |
| 0 542 250 A1 | 5/1993 | European Pat. Off. . |
| 0622420 | 4/1994 | European Pat. Off. . |
| 0 656 363 A1 | 6/1995 | European Pat. Off. . |
| 19522144 | 11/1997 | Germany . |
| 1141868 | 2/1969 | United Kingdom . |

OTHER PUBLICATIONS

Zh. Organ. Khim. 1(9), 1536–9 (1965) (Hussian).
Chemical Abstracts vol. 64, 1966, 628 C1.
Derwent Abstract corresponding to DE 19522144 A1.
L.F. Miqheeva, Bd. 1, No. 9, 1965, pp. 1536–1539, New York, US.

*Primary Examiner*—David W. Wu
*Assistant Examiner*—Tanya Zalukawa
*Attorney, Agent, or Firm*—Brooks & Kushman P.C.

[57] ABSTRACT

The invention describes crosslinkable compositions comprising (1) organosilicon compounds which contain radicals having aliphatic carbon-carbon multiple bonds, (2) organosilicon compounds having Si-bonded hydrogen atoms or, in place of or in addition to (1) and (2); said composition further comprising (3) organosilicon compounds which contain radicals having aliphatic carbon-carbon multiple bonds and Si-bonded hydrogen atoms, (4) catalysts which promote the addition of Si-bonded hydrogen to aliphatic multiple bonds, and

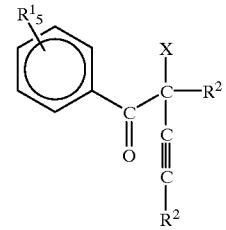

(I)

where $R^1$ and $R^2$ are as defined in claim 1, and X is a radical of the formula —OH, —Cl, —Br and —CN, with the radical —OH being particularly preferred.

20 Claims, No Drawings

CROSSLINKABLE COMPOSITIONS

TECHNOLOGICAL FIELD

The invention relates to crosslinkable compositions comprising
(1) organosilicon compounds which contain radicals having aliphatic carbon-carbon multiple bonds,
(2) organosilicon compounds having Si-bonded hydrogen atoms or, in place of (1) and (2),
(3) organosilicon compounds which contain radicals having aliphatic carbon-carbon multiple bonds and Si-bonded hydrogen atoms,
(4) catalysts which promote the addition of Si-bonded hydrogen onto aliphatic multiple bonds, and
(5) agents which inhibit the addition of Si-bonded hydrogen onto aliphatic multiple bonds at room temperature.

DESCRIPTION OF THE RELATED ART

Organopolysiloxane compositions which can be cured by reaction of SiH groups with Si-bonded olefinic groups in the presence of a hydrosilylation catalyst are known, for example, from U.S. Pat. Nos. 2,813,218, 3,249,581 and 3,436,366. Here, the term hydrosilylation catalysts refers to catalysts which promote the addition of Si-bonded hydrogen onto aliphatic multiple bonds.

Since crosslinking commences on mixing the abovementioned constituents (1), (2) or (3) and (4), it is customary practice to provide addition-crosslinking organopolysiloxane compositions in two components, of which one comprises the olefinically unsaturated organopolysiloxane and the hydrosilylation catalyst and the other comprises the organohydrogenpolysiioxane crosslinker.

If it is necessary to increase the pot life of addition-crosslinking organopolysiloxane compositions or to provide a one-component addition-crosslinking organopolysiloxane composition, an inhibitor can be present therein.

For the purposes of the present invention, the term "inhibitors" refers to agents which inhibit the addition of Si-bonded hydrogen onto aliphatic multiple bonds at room temperature, i.e. inhibitors are compounds which only allow slow crosslinking of addition-crosslinking organopolysiloxane compositions at room temperature, if appropriate with exclusion of light, but do not effectively inhibit crosslinking at elevated temperatures or under the action of light. Such inhibitors can be deactivated by means of heat or high-energy radiation, or are sufficiently volatile to be driven out of the organopolysiloxane compositions at elevated temperature.

GB-A 1,141,868 (published on Feb. 5, 1969, Dow Corning Corporation) describes organic compounds having at least one —C=C— group as inhibitors. The compounds have a high volatility and as a result have a short pot life at slightly elevated temperatures.

EP-A 622 420 (published on Nov. 2, 1994, Rhone-Poulenc Chimie) describes alkynols of the formula R—(R') C(OH)—C≡CH having long chain alkyl or phenyl radicals as inhibitors; these have low volatility, and as a result have sufficient pot life at slightly elevated temperatures. Inhibitors having acetylenic α-keto groups are described in U.S. Pat. No. 4,595,739 (issued on Jun. 17, 1986, Rhone-Poulenc Specialites).

Silicone compositions which can be cured by means of UV light are described in U.S. Pat. No. 4,670,531 (issued on Jun. 2, 1987, General Electric Company); in these compositions, the photolabile inhibitor contains an azo group with an electron-withdrawing group in the a position. These inhibitors have a low molar extinction coefficient and are also thermolabile.

U.S. Pat. No. 5,082,871 (issued on Jan. 21, 1992, General Electric Company) describes dialkyl acetylenecarboxylates as photolabile inhibitors in UV-curable silicone compositions. These inhibitors likewise have a low molar extinction coefficient and a low photolysis rate.

SUMMARY OF THE INVENTION

It is an object of the present invention to provide inhibitors which have but a low volatility and which have a good thermal stability, which ensure sufficiently long inhibition of the crosslinking of the addition-crosslinking compositions based on organosilicon compounds at room temperature, but which decompose photolytically under the action of high-energy radiation and then allow complete crosslinking of the addition-crosslinking compositions based on organosilicon compounds. These and other objects are achieved by the invention.

DESCRIPTION OF THE PREFERRED EMBODIMENT

The invention provides crosslinkable compositions comprising
(1) organosilicon compounds which contain radicals having aliphatic carbon-carbon multiple bonds,
(2) organosilicon compounds having Si-bonded hydrogen atoms or, in place of (1) and (2),
(3) organosilicon compounds which contain radicals having aliphatic carbon-carbon multiple bonds and Si-bonded hydrogen atoms,
(4) catalysts which promote the addition of Si-bonded hydrogen onto aliphatic multiple bonds, and
(5) agents which inhibit the addition of Si-bonded hydrogen onto aliphatic multiple bonds at room temperature, and have the formula

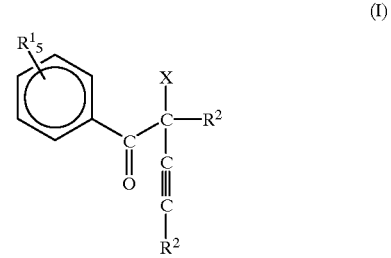

(I)

where $R^1$ are identical or different and are each a hydrogen atom or a monovalent, saturated or unsaturated, substituted or unsubstituted hydrocarbon radical having from 1 to 12 carbon atom(s) per radical, which may be interrupted by an oxygen atom, or a radical of the formula —CN, —SH, —OH, —Cl, —Br, —OR, —O—C(O)—R, —C(O)OR, —SR, —NH$_2$, —NH—R, —C(O)NHR, —NH—C(O)—R, —COOH, where R is a monovalent hydrocarbon radical having from 1 to 12 carbon atom(s) per radical, $R^2$ are identical or different and are each a hydrogen atom or a monovalent, saturated or unsaturated, substituted or unsubstituted hydrocarbon radical having from 1 to 12 carbon atom(s) per radical, which may be interrupted by an oxygen atom, and X is a radical of the formula —OH, —Cl, —Br and —CN, with particular preference being given to the radical —OH.

Examples of hydrocarbon radicals $R^1$ and $R^2$ are alkyl radicals such as the methyl, ethyl, n-propyl, iso-propyl, 1-n-butyl, 2-n-butyl, iso-butyl, tert-butyl, n-pentyl, iso-pentyl, neo-pentyl or tert-pentyl radicals; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; cycloalkyl radicals such as the cyclopentyl, cyclohexyl, cycloheptyl radicals and methylcyclohexyl radicals; aryl radicals such as the phenyl, naphthyl, anthryl and phenanthryl radicals; alkaryl radicals such as o-, m-, p-tolyl radicals; xylyl radicals and ethylphenyl radicals; and aralkyl radicals such as the benzyl radical and the α- and β-phenylethyl radicals. Preference is given to hydrogen atoms and methyl radicals.

Examples of substituted hydrocarbon radicals $R^1$ and $R^2$ are halogenated hydrocarbon radicals. Examples of halogenated hydrocarbon radicals $R^1$ and $R^2$ are haloalkyl radicals such as the 3,3,3-trifluoro-n-propyl radical, the 2,2,2,2',2',2'-hexafluoroisopropyl radical or the heptafluoroisopropyl radical, and haloaryl radicals such as the o-, m- and p-chlorophenyl radicals.

Examples of hydrocarbon radicals $R^1$ and $R^2$ which are interrupted by an oxygen atom are the methoxyethyl and ethoxyethyl radicals.

Examples of hydrocarbon radicals R are alkyl radicals such as the methyl, ethyl, n-propyl, iso-propyl, 1-n-butyl, 2-n-butyl, iso-butyl, tert-butyl, n-pentyl, iso-pentyl, neo-pentyl or tert-pentyl radicals; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; cycloalkyl radicals such as the cyclopentyl, cyclohexyl, cycloheptyl radicals and methylcyclohexyl radicals; aryl radicals such as the phenyl, naphthyl, anthryl and phenanthryl radicals; alkaryl radicals such as o-, m-, p-tolyl radicals; xylyl radicals and ethylphenyl radicals; and aralkyl radicals such as the benzyl radical and the α- and β-phenylethyl radical.

Preferred examples of the inhibitors (5) according to the invention are compounds of the formulae

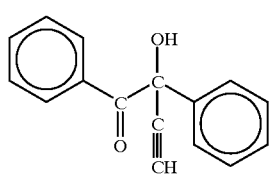

(1)

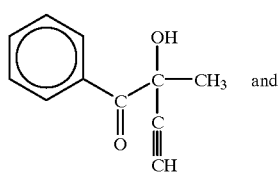 and (2)

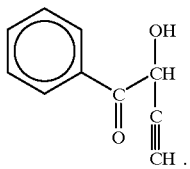

(3)

Compound 1) is 1,2-diphenyl-2-hydroxybut-3-yn-1-one.
Compound 2) is 2-hydroxy-2-methyl-1-phenylbut-3-yn-1-one.
Compound 3) is 2-hydroxy-1-phenylbut-3-yn-1-one.
Compound 1) is described by L. F. Mikheeva in Zh. Organ. Khim 1(9), 1536 (1965).

The inhibitors according to the invention are prepared by a method analogous to that described in Zh. Organ. Khim 1 (9), 1536 (1965).

The inhibitors employed according to the invention and having the formula (I) are preferably used in amounts of from 0.1% by weight to 1.5% by weight, particularly preferably in amounts of from 0.3% by weight to 0.7% by weight, based on the total weight of the organosilicon compounds (1) and (2) or on the total weight of the organosilicon compound (3).

The inhibitors according to the invention can be mixed beforehand with the organosilicon compounds (1), (2) or (3) or with the catalyst component (4).

The compositions of the invention comprising the constituents (1), (2) or (3), (4) and (5) are preferably provided in the form of two-component compositions, with the constituents (2) or (3) and (4) being kept separate from one another.

The inhibitors of the formula (I) can be used in all crosslinkable compositions in which inhibitors which inhibit the addition of Si-bonded hydrogen onto aliphatic multiple bonds at room temperature have also been used hitherto.

As organopolysiloxanes (1) which contain radicals having aliphatic carbon-carbon multiple bonds, preference is given to using linear or branched organopolysiloxanes comprising units of the formula (II)

(II)

where $R^3$ is a monovalent, substituted or unsubstituted hydrocarbon radical which is free of aliphatic carbon-carbon multiple bonds and has from 1 to 18 carbon atoms per radical and $R^4$ is a monovalent hydrocarbon radical having a terminal, aliphatic carbon-carbon multiple bond and from 2 to 8 carbon atoms per radical, a is 0, 1, 2 or 3, b is 0, 1 or 2 and the sum a+b is 0, 1, 2 or 3, with the proviso that on average at least two radicals $R^4$ are present.

Preferred organosilicon compounds (1) are organopolysiloxanes of the formula

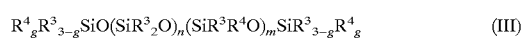

(III)

where $R^3$ and $R^4$ are as defined above, g is 0, 1 or 2, n is 0 or an integer from 1 to 1500 and m is 0 or an integer from 1 to 200, with the proviso that on average at least two radicals $R^4$ are present.

For the purposes of the present invention, formula (III) should be interpreted such that n units —(SiR$^3{}_2$O)— and m units —(SiR$^3$R$^4$O)— can be distributed in any manner in the organopolysiloxane molecule.

Other organosilicon compounds (1) which can be used are siloxane copolymers as are described in U.S. Pat. No. 5,241,034 and in DE-A 195 22 144 and comprise siloxane blocks and hydrocarbon blocks.

The organopolysiloxanes (1) preferably have an average viscosity of from 100 to 10,000 mPa·s at 25° C.

Examples of hydrocarbon radicals $R^3$ are alkyl radicals such as the methyl, ethyl, n-propyl, iso-propyl, n-butyl, iso-butyl, tert-butyl, n-pentyl, iso-pentyl, neo-pentyl or tert-pentyl radicals; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical, dodecyl radicals such as the n-dodecyl radical; octadecyl radicals such as the n-octadecyl radical; cycloalkyl radicals such as cyclopentyl, cyclohexyl and cycloheptyl radicals and methylcyclohexyl radicals; aryl radicals such as the phenyl, naphthyl, anthryl and phenanthryl radicals; alkaryl radicals such as o-, m-, p-tolyl radicals, xylyl radicals and ethylphenyl radicals; and aralkyl radicals such as the benzyl radical, the α- and β-phenylethyl radical.

Examples of radicals $R^4$ are alkenyl radicals such as the vinyl, 5-hexenyl, allyl, 3-butenyl and 4-pentenyl radicals; and alkynyl radicals such as the ethynyl, propargyl and 1-propynyl radicals.

As organosiloxanes (2) having Si-bonded hydrogen atoms, preference is given to using linear, cyclic or branched organopolysiloxanes comprising units of the formula (IV)

where $R^3$ is as defined above, e is 0, 1, 2 or 3, f is 0, 1 or 2 and the sum of e+f is 0, 1, 2 or 3, with the proviso that on average at least two Si-bonded hydrogen atoms are present.

The organosilicon compounds (2) used are preferably organopolysiloxanes of the formula $$H_hR^3{}_{3-h}SiO(SiR^3{}_2O)_o(SiR^3HO)_pSiR^3{}_{3-h}H_h \quad (V)$$

where $R^3$ is as defined above, h is 0, 1 or 2, o is 0 or an integer from 1 to 1500 and p is 0 or an integer from 1 to 200, with the proviso that on average at least two Si-bonded hydrogen atoms are present.

For the purposes of the present invention, formula (V) should be interpreted such that o units —(SiR$^3{}_2$O)— and p units —(SiR$^3$HO)— can be distributed in any manner in the organopolysiloxane molecule.

The organopolysiloxanes (2) preferably have an average viscosity of from 10 to 1000 mPa·s at 25° C.

Organosilicon compound (2) is preferably used in amounts of from 0.8 to 3.0, preferably from 1.5 to 2.5 gram atoms of Si-bonded hydrogen per mole of Si-bonded radical having an aliphatic carbon-carbon multiple bond in the organosilicon compound (1).

As organopolysiloxanes (3) which contain aliphatic carbon-carbon multiple bonds and Si-bonded hydrogen atoms and can be used in place of organopolysiloxanes (1) and (2), preference is given to using those comprising units of the formulae

and

where $R^3$ and $R^4$ are as defined above, k is 0, 1, 2 or 3, l is 0, 1 or 2, d is 0, 1 or 2, with the proviso that on average at least two radicals $R^4$ and on average at least two Si-bonded hydrogen atoms are present.

Examples of organopolysiloxanes (3) are organopolysiloxanes comprising SiO$_{4/2}$, $R^3{}_3$SiO$_{1/2}$, $R^3{}_2R^4$SiO$_{1/2}$ and $R^3{}_2$HSiO$_{1/2}$ units, known as MQ resins, where these resins can comprise T units ($R^3$SiO$_{3/2}$) and D units ($R^4{}_2$SiO). The organopolysiloxanes (3) preferably have an average viscosity of from 100 to 100,000 mPa·s at 25° C. or are solids having molecular weights of from 5000 to 50,000 g/mol. It is also possible to use mixtures of (1), (2), and (3) as long as the crosslinkable composition contains both alkenyl and SiH functionality, and the claims should be so interpreted.

As catalysts which promote the addition of Si-bonded hydrogen onto aliphatic multiple bonds, it is also possible to use, in the process of the invention, the same catalysts which have also been able to be used hitherto for promoting the addition of Si-bonded hydrogen onto aliphatic multiple bonds.

The catalysts are preferably a metal of the platinum metal group or a compound or a complex of a platinum group metal, e.g. platinum, palladium or rhodium, preferably a compound or a complex of platinum.

Examples of such catalysts are metallic and finely divided platinum which may be located on supports such as silicon dioxide, aluminum oxide or activated carbon, compounds or complexes of platinum, for example platinum halides such as PtCl$_4$, H$_2$PtCl$_6$*6H$_2$O, Na$_2$PtCl$_4$*4H$_2$O, platinum-olefin complexes, platinum-alcohol complexes, platinum-ether complexes, platinum-aldehyde complexes, platinum-ketone complexes, including reaction products of H$_2$PtCl$_6$*6H$_2$O and cyclohexanone, platinum-vinylsiloxane complexes such as platinum-1,3-divinyl-1,1,3,3-tetramethyldisiloxane complexes with or without a content of detectable inorganically bound halogen, bis(gamma-picoline)platinum dichloride, trimethylenedipyridineplatinum dichloride, dicyclopentadieneplatinum dichloride, (dimethyl sulfoxide)ethyleneplatinum(II) dichloride, cyclooctadieneplatinum dichloride, norbornadieneplatinum dichloride, (gamma-picoline)platinum dichloride, cyclopentadieneplatinum dichloride and also reaction products of platinum tetrachloride with olefin and primary amine or secondary amine or primary and secondary amine as described in U.S. Pat. No. 4,292,434, for example the reaction product of platinum tetrachloride dissolved in 1-octene with sec-butylamine, or ammonium-platinum complexes as described in EP-B 1 10 370.

The catalysts (4) are preferably used in amounts of from 5 to 300 ppm by weight (parts by weight per million parts by weight), preferably from 20 to 200 ppm by weight, in each case calculated as elemental platinum metal and based on the total weight of the organosilicon compounds (1) and (2) or on the total weight of the organosilicon compound (3).

The compositions of the invention are preferably cured at the pressure of the surrounding atmosphere, i.e. at about 1020 hPa (abs.), but they can also be cured at higher or lower pressures.

The compositions of the invention can be crosslinked under the action of high-energy radiation. Many types of radiation are suitable for this purpose, for example electron beams, γ-rays, X-rays, UV light such as that having a wavelength in the range from 200 to 400 nm, and visible light such as that having a wavelength of from 400 to 600 nm, i.e. "halogen light". Ultraviolet light can be produced, for example, in xenon, mercury low-pressure, mercury medium-pressure or mercury high-pressure lamps and excimer lamps. The high-energy radiation by means of which the compositions of the invention are crosslinked is preferably UV light having a wavelength in the range from 200 to 400 nm.

The compositions of the invention can also be crosslinked purely thermally without exposure to high-energy radiation, which is why they have only a limited shelf life when such radiation is excluded. However, this time, known as the pot life, is many times the crosslinking time under the action of high-energy radiation, which is why purely thermal curing is, although possible, not preferred.

The organopolysiloxane preparations of the invention can further comprise the inhibitors mentioned in the prior art, although their concomitant use is not preferred.

In the compositions of the invention, it is possible to make additional use of inert, organic solvents, although the concomitant use of inert, organic solvents is not preferred. Examples of inert, organic solvents are toluene, xylene, isophorone, octane isomers, n-butyl acetate and isopropanol.

In addition, the compositions of the invention can further comprise additives such as fillers, pigments and coupling agents such as silanes or epoxide compounds.

The compositions of the invention can be used wherever crosslinkable compositions based on addition-curing silicone preparations have also been used hitherto. For example, the compositions of the invention are extremely well suited to producing solid coatings or moldings. Examples of surfaces to which the coatings according to the invention can be applied are those of paper, wood, cork, plastic films, e.g. polyethylene films or polypropylene films, ceramic articles, glass, including glass fibers, metals, board, including that made of asbestos, and of woven and non-woven cloth made of natural or synthetic organic fibers.

The application of the organosilicon preparations of the invention to the surfaces to be coated can be carried out in any frequently known way which is suitable for the production of coatings from liquid materials, for example by dipping, painting, casting, spraying, rolling on, printing, e.g. by means of an offset gravure coating apparatus, a knife or double blade coater. In particular, the compositions of the invention are suitable for use in adhesive coating compositions such as release paper coatings, coatings generally, and in electronics.

In the following examples, all parts and percentages are, unless otherwise indicated, by weight. Unless otherwise indicated, the following examples are carried out at the pressure of the surrounding atmosphere, i.e. at about 1000 hPa, and at room temperature, i.e. at about 20° C., or at a temperature which is established on combining the reactants at room temperature without additional heating or cooling. In the following, all viscosities are based on a temperature of 25° C.

EXAMPLE 1 a) 10.51 g (0.05 mol) of benzil are dissolved in 30 g of THF (tetrahydrofuran) and cooled while stirring to 0° C. 100 ml of a 0.5 molar solution (0.05 mol) of ethynylmagnesium chloride in THF are added dropwise under a nitrogen atmosphere over a period of 45 minutes at such a rate that the temperature does not exceed 0° C. After stirring for 30 minutes at 3° C., stirring is continued for 24 hours at room temperature. 1.8 ml (0.1 mol) of water are then added dropwise and the mixture is stirred further for one hour. The suspension is admixed with 10 g (0.084 mol) of anhydrous sodium sulfate, stirred for one hour and then filtered. The filtrate is evaporated to constant weight at 40° C. in a high vacuum. The brown, sticky crude product is dissolved at the boiling point in a mixture of 40 ml of n-hexane and 10 ml of diethyl ether, filtered and slowly crystallized. The solid is filtered off, dried and recrystallized once more by the abovementioned method. This gives 5.1 g (43% of theory) of 1,2-diphenyl-2-hydroxybut-3-yn-1-one in the form of a yellow, finely crystalline solid (inhibitor 1).

b) 0.194 g ($8.21 \times 10^{-4}$ mol) of inhibitor 1, whose preparation has been described above under a), are dissolved in 1 ml of toluene and then added to 40 g of α,ω-divinyldimethylpolysiloxane having a viscosity of 500 mPa·s at 25° C. The solvent is removed at room temperature under reduced pressure. 1.05 g of a copolymer comprising trimethylsiloxane and methyl-hydrogensiloxane units, having a viscosity of 33 mPa·s at 25° C. and containing 1.12% by weight of Si-bonded hydrogen are added to the remaining reaction mixture. Finally, while stirring, 0.4 g (100 ppm of platinum, based on pure metal and total mixture) of a 1% strength by weight solution of a divinyltetramethyldisiloxaneplatinum(0) complex in α,ω-divinyldimethylpolysiloxane having a viscosity of 1000 mPa·s at 25° C. is metered in.

The gel times of the abovementioned mixture at various temperatures are summarized in Table 1. They were determined by means of a gel timer from Bachhofer at a fill height of 10 cm.

TABLE 1

| Temperature (° C.) | Gel Times (min) |
| --- | --- |
| 25 | 2866 |
| 60 | 41 |
| 100 | 4 |

In addition, the above-mentioned mixture was spread in a thickness of about 3 μm on a PE-coated paper from PWA Raubling by means of a glass rod and was irradiated for 18 seconds with ultraviolet light (UVA—56 mW/cm$^2$, UVB—12 mW/cm$^2$) at 560° C.

This gave a transparent coating which was insoluble in organic solvents and contained less than 5% by weight of uncrosslinked materials.

EXAMPLE 2 a) 7.41 g (0.05 mol) of phenylpropanedione are dissolved in 30 g of THF and cooled while stirring to 0° C. 100 ml of a 0.5 molar solution (0.05 mol) of ethynyl magnesium chloride in THF are added dropwise under a nitrogen atmosphere over a period of 30 minutes at such a rate that the temperature does not exceed 0° C. The reaction solution is then stirred further for 48 hours at room temperature. The clear, dark brown solution is now admixed with 1.8 ml (0.1 mol) of water and stirred for one hour at room temperature. After drying over anhydrous sodium sulfate, it is filtered and the THF is removed by distillation. The brown, liquid residue is fractionally distilled in a high vacuum at up to 180° C. The boiling range of the main fraction is from 153° C. to 161° C. This gives 2.4 g (28% of theory) of 2-hydroxy-2-methyl-1-phenylbut-3-yn-1-one in the form of a yellow liquid (inhibitor 2).

b) 0.143 g (8.22×10$^{-4}$ mol) of inhibitor 2, whose preparation has been described above under a), is dissolved in 1 ml of toluene and then added to 40 g of α,ω-divinyldimethylpolysiloxane having a viscosity of 500 mPa·s at 25° C. The solvent is removed at room temperature under reduced pressure. 1.05 g of a copolymer comprising trimethylsiloxane and methylhydrogensiloxane units, having a viscosity of 33 mPa·s at 25° C. and containing 1.12% by weight of Si-bonded hydrogen are added to the reaction mixture. Finally, while stirring, 0.4 g (100 ppm of platinum, based on pure metal and total mixture) of a 1% strength by weight solution of a divinyltetramethyldisiloxaneplatinum (0) complex in α,ω-divinyldimethylpolysiloxane having a viscosity of 1000 mPa·s at 25° C. is metered in.

The gel times of the abovementioned mixture at various temperatures are summarized in Table 2. They were determined using a gel timer from Bachhofer at a fill height of 10 cm.

TABLE 2

| Temperature (° C.) | Gel Times (min) |
| --- | --- |
| 25 | 17,560 |
| 60 | 287 |
| 100 | 6 |

In addition, the above-mentioned mixture was spread in a thickness of about 3 μm on a PE-coated paper from PWA Raubling by means of a glass rod and was irradiated for 16 seconds with ultraviolet light (UVA—56 mW/cm$^2$, UVB—12 mW/cm$^2$) at 56° C. This gave a transparent coating which was insoluble in organic solvents and contained less than 5% by weight of uncrosslinked materials.

What is claimed is:

1. A crosslinkable composition comprising
   (1) organosilicon compounds which contain radicals having aliphatic carbon-carbon multiple bonds,
   (2) organosilicon compounds having Si-bonded hydrogen atoms or, in place of (1) and (2),
   (3) organosilicon compounds which contain radicals having aliphatic carbon-carbon multiple bonds and Si-bonded hydrogen atoms; said composition further comprising
       (4) catalysts which promote the addition of Si-bonded hydrogen to aliphatic multiple bonds, and
       (5) agents which inhibit the addition of Si-bonded hydrogen to aliphatic multiple bonds at room temperature, said agents having the formula

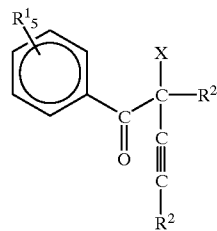

(I)

where R$^1$ are identical or different and are each a hydrogen atom or a monovalent, saturated or unsaturated, substituted or unsubstituted hydrocarbon radical having from 1 to 12 carbon atom(s) per radical, which may be interrupted by an ether oxygen atom, or are a radical of the formula —CN, —SH, —OH, —Cl, —Br, —OR, —O—C(O)—R, —C(O)OR, —SR, —NH$_2$, —NH—R, —C(O)NHR, —NH—C(O)—R, —COOH, where R is a monovalent hydrocarbon radical having from 1 to 12 carbon atom(s) per radical, R$^2$ are identical or different and are each a hydrogen atom or a monovalent, saturated or unsaturated, substituted or unsubstituted hydrocarbon radical having from 1 to 12 carbon atom(s) per radical, which may be interrupted by an ether oxygen atom, and X is a radical of the formula —OH, —Cl, —Br and —CN.

2. A crosslinkable composition as claimed in claim 1, wherein X is a radical of the formula —OH.

3. A crosslinkable composition as claimed in claim 1, wherein the agent (5) which inhibits the addition of Si-bonded hydrogen to aliphatic multiple bonds at room temperature is 1,2-diphenyl-2-hydroxybut-3-yn-1-one.

4. A crosslinkable composition as claimed in claim 1, wherein the agent (5) which inhibits the addition of Si-bonded hydrogen to aliphatic multiple bonds at room temperature is 2-hydroxy-2-methyl-1-phenylbut-3-yn-1-one.

5. A process for producing coatings which repel sticky materials, said process comprising applying a crosslinkable composition as claimed in claim 1 to a surface to be made repellant to sticky materials and subsequently curing the composition.

6. A process for producing coatings which repel sticky materials, said process comprising applying a crosslinkable composition as claimed in claim 2 to a surface to be made repellant to sticky materials and subsequently curing the composition.

7. A process for producing coatings which repel sticky materials, said process comprising applying a crosslinkable composition as claimed in claim 3 to a surface to be made repellant to sticky materials and subsequently curing the composition.

8. A process for producing coatings which repel sticky materials, said process comprising applying a crosslinkable composition as claimed in claim 4 to a surface to be made repellant to sticky materials and subsequently curing the composition.

9. A process for producing coatings which repel sticky materials, said process comprising
   applying the crosslinkable composition of claim 1 to a surface to be made repellant to sticky materials;
   exposing said crosslinkable composition to high energy radiation; and thermally curing said crosslinkable composition, wherein said step of thermally curing takes place concurrently with or subsequent to said step of exposing, and wherein said step of exposing causes photolytic decomposition of said inhibitor, such that the cure time is reduced thereby.

10. A process for producing coatings which repel sticky materials, said process comprising applying the crosslinkable composition of claim 2 to a surface to be made repellant to sticky materials;

exposing said crosslinkable composition to high energy radiation; and thermally curing said crosslinkable composition, wherein said step of thermally curing takes place concurrently with or subsequent to said step of exposing, and wherein said step of exposing causes photolytic decomposition of said inhibitor, such that the cure time is reduced thereby.

11. process for producing coatings which repel sticky materials, said process comprising applying the crosslinkable composition of claim 3 to a surface to be made repellant to sticky materials;

exposing said crosslinkable composition to high energy radiation; and thermally curing said crosslinkable composition, wherein said step of thermally curing takes place concurrently with or subsequent to said step of exposing, and wherein said step of exposing causes photolytic decomposition of said inhibitor, such that the cure time is reduced thereby.

12. A process for producing coatings which repel sticky materials, said process comprising applying the crosslinkable composition of claim 4 to a surface to be made repellant to sticky materials;

exposing said crosslinkable composition to high energy radiation; and thermally curing said crosslinkable composition, wherein said step of thermally curing takes place concurrently with or subsequent to said step of exposing, and wherein said step of exposing causes photolytic decomposition of said inhibitor, such that the cure time is reduced thereby.

13. In a crosslinkable composition comprising an organosilicon compound having aliphatic carbon-carbon multiple bands, an Si—H functional organosilicon compound, a hydrosilylation catalyst, and an inhibitor of hydrosilylation, the improvement comprising selecting as an inhibitor, an inhibitor whose inhibitory effect decreases on exposure to high energy radiation, thereby allowing crosslinking of said crosslinkable composition by hyrosilylation, said inhibitor having the formula

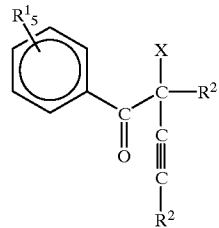

where $R^1$ are identical or different and are each a hydrogen atom or a monovalent, saturated or unsaturated, substituted or unsubstituted hydrocarbon radical having from 1 to 12 carbon atom(s) per radical, which may be interrupted by an oxygen atom, or are a radical of the formula —CN, —SH, —OH, —Cl, —Br, —OR, —O—C(O)—R, —C(O)OR, —SR, —NH$_2$, —NH—R, —C(O)NHR, —NH—C(O)—R, —COOH, where R is a monovalent hydrocarbon radical having from 1 to 12 carbon atom(s) per radical, $R^2$ are identical or different and are each a hydrogen atom or a monovalent, saturated or unsaturated, substituted or unsubstituted hydrocarbon radical having from 1 to 12 carbon atom(s) per radical, which may be interrupted by an oxygen atom, and X is a radical of the formula —OH, —Cl, —Br and —CN.

14. A crosslinkable composition as claimed in claim 13, wherein X is a radical of the formula —OH.

15. A crosslinkable composition as claimed in claim 13, wherein said inhibitor is 1,2-diphenyl-2-hydroxybut-3-yn-1-one.

16. A crosslinkable composition as claimed in claim 13, wherein said inhibitor is 2-hydroxy-2-methyl-1-phenylbut-3-yn-1-one.

17. The crosslinkable composition as claimed in claim 1, wherein said agent(s) (5) are present in an amount of 0.1 weight percent to 1.5 weight percent based on the total weight of the organosilicon compounds (1), (2) and (3).

18. The crosslinkable composition as claimed in claim 1, wherein said agent(s) (5) are present in an amount of 0.3 weight percent to 0.7 weight percent based on the total weight of the organosilicon compounds (1), (2) and (3).

19. The crosslinkable composition of claim 13, wherein said inhibitor is present in an amount of 0.1 weight percent to about 1.5 weight percent based on the total weight of said organosilicon compounds having aliphatic carbon-carbon multiple bonds and said Si—H functional organosilicon compounds.

20. The crosslinkable composition of claim 13, wherein said inhibitor is present in an amount of 0.3 weight percent to about 0.7 weight percent based on the total weight of said organosilicon compounds having aliphatic carbon-carbon multiple bonds and said Si—H functional organosilicon compounds.

* * * * *